(12) United States Patent
Apostolos et al.

(10) Patent No.: US 9,052,370 B2
(45) Date of Patent: Jun. 9, 2015

(54) DETECTION PROCESSING FOR NQR SYSTEM

(71) Applicant: AMI Research & Development, LLC, Windham, NH (US)

(72) Inventors: John T. Apostolos, Lyndeborough, NH (US); Judy Feng, Nashua, NH (US); William Mouyos, Windham, NH (US)

(73) Assignee: AMI Research & Development, LLC, Windham, NH (US)

( * ) Notice: Subject to any disclaimer, the term of this patent is extended or adjusted under 35 U.S.C. 154(b) by 0 days.

(21) Appl. No.: 14/206,394

(22) Filed: Mar. 12, 2014

(65) Prior Publication Data

US 2014/0266209 A1    Sep. 18, 2014

Related U.S. Application Data

(60) Provisional application No. 61/781,691, filed on Mar. 14, 2013, provisional application No. 61/816,875, filed on Apr. 29, 2013, provisional application No. 61/869,343, filed on Aug. 23, 2013.

(51) Int. Cl.
*G01R 33/36* (2006.01)
*G01N 24/08* (2006.01)
*G01R 33/44* (2006.01)

(52) U.S. Cl.
CPC .......... *G01R 33/3621* (2013.01); *G01N 24/084* (2013.01); *G01R 33/441* (2013.01)

(58) Field of Classification Search
CPC . G01N 24/084; G01R 33/3621; G01R 33/441

USPC .............................. 324/300–322; 702/23–38
See application file for complete search history.

(56) References Cited

U.S. PATENT DOCUMENTS

| | | | |
|---|---|---|---|
| 5,457,385 A | 10/1995 | Sydney et al. |
| 5,592,083 A | 1/1997 | Magnuson et al. |
| 5,814,987 A | 9/1998 | Smith et al. |
| 6,100,688 A | 8/2000 | Smith et al. |
| 6,127,824 A | 10/2000 | Smith et al. |
| 6,392,408 B1 | 5/2002 | Barrall et al. |
| 7,999,541 B2 | 8/2011 | Chisholm et al. |

(Continued)

FOREIGN PATENT DOCUMENTS

| | | | |
|---|---|---|---|
| JP | 2009 264972 A | 11/2009 |
| WO | WO 2011/094462 A1 | 8/2011 |

(Continued)

OTHER PUBLICATIONS

Peshkovsky A. S. et al. "Noise-resilient multi-frequency surface sensor for nuclear quadrupole resonance," Journal of Magnetic Resonance, Academic Press, Orlando, FL, vol. 194, No. 2, Oct. 1, 2008, pp. 222-229.

(Continued)

*Primary Examiner* — Melissa Koval
*Assistant Examiner* — Rishi Patel
(74) *Attorney, Agent, or Firm* — Cesari and McKenna, LLP

(57) ABSTRACT

A system that uses the nuclear quadrupole resonant effect to detect the presence of materials of interest, such as may be excited by radio frequency fields generated within a portal. Transmitted chirp signals may be processed using matching filtering and other signal processing to accurately detect the presence of such materials.

10 Claims, 7 Drawing Sheets

(56) References Cited

U.S. PATENT DOCUMENTS

| 8,660,803 B2 | 2/2014 | Apostolos et al. | |
|---|---|---|---|
| 8,901,926 B2 * | 12/2014 | Apostolos et al. | 324/300 |
| 8,912,788 B2 * | 12/2014 | Apostolos et al. | 324/204 |
| 2006/0140249 A1 | 6/2006 | Kohno | |
| 2007/0018644 A1 | 1/2007 | Flexman et al. | |

FOREIGN PATENT DOCUMENTS

| WO | WO 2011/094463 A1 | 8/2011 |
|---|---|---|
| WO | WO 2011/094466 A1 | 8/2011 |
| WO | WO 2011/102948 A1 | 8/2011 |
| WO | WO 2011/126594 A2 | 10/2011 |
| WO | WO 2011/152887 A2 | 12/2011 |
| WO | 2013049270 | 4/2013 |

OTHER PUBLICATIONS

International Search Report and Written Opinion, mail date Dec. 20, 2012 for International Application No. PCT/US2012/057425, International Filing Date Sep. 27, 2012, AMI Research & Development, Inc. 15 pages.

Itozaki et al. "Nuclear Quadrupole Resonance for Explosive Detection" Graduate School of Engineering Science, Osaka, 560-8531, Japan, International Journal on Smart Sensing and Intelligent Systems, vol. 1, No. 3, Sep. 2008, pp. 705-715.

Apostolos, John T., et al., "Low-power stimulated emission nuclear quadrupole resonance detection system utilizing Rabi transitions," Proceedings of SPIE, SPIE—International Society for Optical Engineering, US, vol. 8709, Jun. 7, 2013, pp. 87090Q-1.

Hyde, J.S. et al., "W-band frequency-swept EPR" Journal of Magnetic Resonance, Academic Press, Orlando, FL,US, vol. 205, No. 1, Jul. 1, 2010, pp. 93-101.

Gupta, R. K. et al., "Rapid scan Fourier transform NMR spectroscopy," Journal of Magnetic Resonance, Academic Press, London, GB, vol. 13, No. 3, Mar. 1, 1974, pp. 275-290.

International Search Report and Written Opinion mail date Jul. 30, 2014 for International Patent Application No. PCT/US2014/025196 filed on Mar. 13, 2014 by AMI Research & Development, LLC, 15 pages.

* cited by examiner

DETECTION PROCESSING FOR NQR SYSTEM

CROSS REFERENCE TO RELATED APPLICATIONS

This application claims the benefit of U.S. Provisional Application Ser. No. 61/781,691 filed on Mar. 14, 2013, U.S. Provisional Application Ser. No. 61/816,875 filed on Apr. 29, 2013, and U.S. Provisional Application Ser. No. 61/869,343 filed on Aug. 23, 2013. The entire contents of each of those applications are hereby incorporated by reference.

BACKGROUND

1. Technical Field

This application relates to chemical analysis and more particularly to systems and methods that use the nuclear quadrupole resonance effect to detect certain types of materials.

2. Background

Systems that use the Nuclear Quadrupole Resonance (NQR) effect to detect the existence of certain materials are known in the art. One example system was described in U.S. Pat. No. 8,660,803 assigned to AMI Research and Development, LLC, the assignee of this application, hereby incorporated by reference. These systems use one or more conductive surfaces to define a space or portal that is to be monitored. Two or more wire loops are disposed within the space typically adjacent the conductive surfaces. The wire loops are each individually electrically terminated in one arrangement; alternatively, they can be arranged as balanced transmission lines. The wire loops are driven with a radio frequency (RF) transmitter to create time varying electromagnetic fields of various types within the defined space.

The time varying electromagnetic fields stimulate Nuclear Quadrupole Resonance (NQR) in any material with an electric quadrupole moment, thereby causing the material(s) to emit coherent RF emissions. By utilizing Rabi transitions the nucleus of material atoms oscillates between a first and second state, under the time dependent incident electromagnetic field, and alternately absorbs energy from the incident field while emitting coherent energy via stimulated emission. These stimulated emissions are then received. The received RF emissions are then further processed to determine characteristics of the substance, such as by detecting the amplitude, phase and/or frequency, and comparing them to the responses for known materials.

SUMMARY

The resulting NQR resonances involve so-called Rabi transitions, which are non-linear responses to the stimulated emissions. It therefore becomes desirable to design the is excitation RF fields and detectors in such a way as to encourage accurate detection, even in the presence of such non-linear effects.

It can be discerned that a deterministic relationship exists between the RF signal use to excite the electromagnetic fields and the emitted response signal; this relationship depends on the transmitter circuitry used to generate the RF fields. This relationship, if known, can further improve the performance of post detection signal processing.

More specifically, an NQR system illuminates the portal with multiple linear chirp signals at multiple phases and multiple power state. Receive signal processing preferably involves reference signal cancellation, de-chirping, decimation, S21 parameter extraction, interference cancellation, end point decomposition, high and low power measurement correction, and matched filtering.

In one embodiment, the receive signal processing includes end point integration to improve extraction of the S21 parameters.

Another embodiment uses a matched filter synthesized from a transmitted chirp waveform composed of Rabi oscillations.

In yet another embodiment, two chirps are simultaneously emitted as the RF signals, to excite an NQR response at a known third frequency.

BRIEF DESCRIPTION OF THE DRAWINGS

The description below refers to the accompanying drawings, of which.

DETAILED DESCRIPTION OF AN EMBODIMENT

Figure 1:
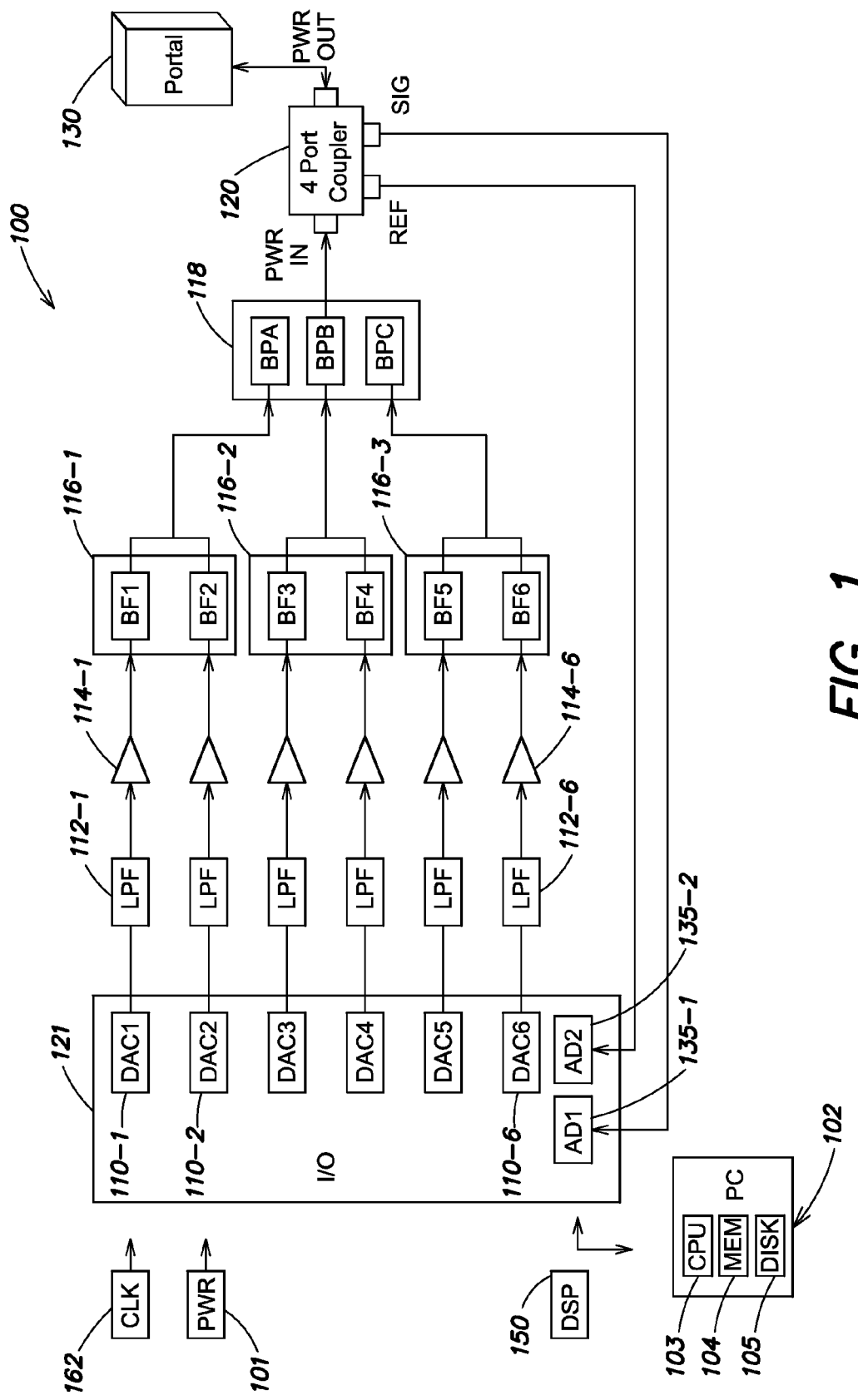
FIG. 1 is a high-level block diagram of an NQR detection system.

FIG. 1 is a high-level diagram of the components of a detection system 100 according to the teachings herein. In general, the system 100 may be controlled by a programmable data processor such as a personal computer (PC) 102 that controls digital and/or analog circuitry to cause electromagnetic fields to be generated in a portal. The PC 102 also controls circuitry that detects and then performs digital signal processing on the resulting responses.

The PC 102 specifically controls generation of one or more suitable radio frequency RF waveform(s) via a set of Digital to Analog Converters (DACs) 110, filters 112, amplifiers 114, RF combining circuits which may include diplexer filters 116, and/or triplexer filters 118. The resulting RF waveform(s) are then provided to an input port (PWR IN) of a single four (4)-port coupler, or other set of couplers. The coupler(s) 120 provide a corresponding output signal (PWR OUT). The signal from the PWR OUT port is coupled to a portal 130 containing the substance to be detected, which may include a human being carrying the substance on or within their person.

Responses from the portal 130 are then returned to the 4-port coupler 120 at a signal port (SIG) of the same four-port coupler 120. A reference signal (REF), also provided by the 4-port coupler, is fed together with the signal received at the SIG port into a pair of Analog to Digital Converters (ADCs) 135-1, 135-2. The outputs from the ADCs 135 are then subjected to signal processing implemented by the Personal Computer 102, and/or some other processor such as a Digital Signal Processor (DSP) 150, to recognize substances of interest which may be located within the portal 130.

The personal computer (PC) 102 may include a typical central processing unit (CPU) 103, memory 104, disk and/or other mass storage devices 105 to store and execute software programs and data that implement the functions described herein. A power supply 101 provides power to the PC 102 as well as to the other components of the system. A clock signal generator 162 also provides a clock signal to the other components of the system. An input/output (I/O) subsystem 121, which may be a peripheral board plugged into the PC 102 via a suitable interface, includes the digital to analog converters 110 (DAC1 to DACE)) and analog to digital converters 135 (AD1 and AD2).

The detection system 100 of FIG. 1 is typically architected with a combination of digital and RF components to apply a combination of linear chirp signals to the portal and detect the resulting NQR emissions. The chirp signals are generated by the PC controlling the Digital to Analog Converters (DACs); each chirp is associated with one or more NQR frequencies of interest. For example, a given chirp waveform may be a linear frequency modulated (FM) sweep. The sweep thus includes a range of frequencies including a chirp start frequency and a chirp stop frequency—the chirp range includes typically, at least one NQR emission frequency of interest. The chirp signal may increase or decrease in frequency over time. Multiple chirp waveforms with different power state illuminations different frequencies, and out/input phases may be generated at any given instant in time via the multiple DACs 110-1, 110-2, ... 110-6 operating in parallel.

The generated chirp signals are then filtered 112, amplified 114, and mulitplexed and/or combined 116, 118 before being sent to the sensing portal 130 to produce a low-power magnetic field.

This magnetic field(s) generated in response to the chirped RF signals are then made incident on whatever is contained in the portal 130, causing coherent NQR emissions from the contents. The response signal(s) from the portal 130 contain the transmitted energy, reflected energy, and the NQR chirp signal(s). This response signal, as received at the SIG port of coupler 120, together with a reference signal from the REF port, are then digitized by the corresponding analog to digital converters (AD1 and AD2) 135-1, 135-2. The digitized response signals are then fed to cancellation and matched filter algorithm(s) executed by the personal computer 102 and/or digital signal processor 150, to make a decision as to whether the portal 130 contains an explosive material of interest or not.

The specific embodiment shown in FIG. 1 uses six (6) amplifiers 114-1, ... 114-6 feeding a set of three (3) diplexers 116 and a triplexer 118, although other arrangements for combining RF signals are possible. This arrangement allows up to six simultaneous chirp signals to be introduced through the 4-port coupler 120 to the portal 130 at a time. Even when there may be multiple materials of interest, it can be desirable that only one quadrupole resonance per candidate material is excited at any given point in time, although at any given point in time, more than one candidate material can be excited.

More details of the quadrupole resonant frequencies of interest, and thus the frequency ranges of the chirp signals needed to detect certain materials are described in is more detail in the patents and patent applications referenced above.

More details of the portal design, excitation wire loops, signal generation, signal detection, and signal processing, as well as alternative system architectures are also described in the patents and patent applications that referenced above.

FIGS. 2 through 6 contain a more detailed view of the receive signal processing functions of the system. It is understood that the signal processing functions may be implemented by digital hardware circuitry, and/or via software programs operating the digital signal processor 150, and/or the personal computer 102, and/or hardware accelerators associated with the personal computer 102, or some combination of two or more of these implementation options.

To develop enough cancellation to deal with NQR signals at levels of less than −70 dBm buried in an incident field of 40 dBm, a combination of directional couplers and a two (2) channel base band digital receiver is utilized. The cancellation methodology employs a waveform with alternating two (2) power state illuminations which are combined to cancel the incident field. The frequency range of interest covered is approximately 330 KHz to 5 MHz. As explained above, the transmit waveforms utilized are a continuous linear, frequency modulated (FM) chirp to provide frequency agility and facilitate the use of a matched filter for the NQR response to the chirp. The wideband chamber was designed and built with the necessary performance, and generates fields that are in the 10 W/m2 range with low leakage beyond the chamber. The test chamber used to validate the technology is 30.0 inches wide by 30.0 inches high by 36.0 inches deep and was used for all the experimental measurements presented in this paper.

Figure 2:
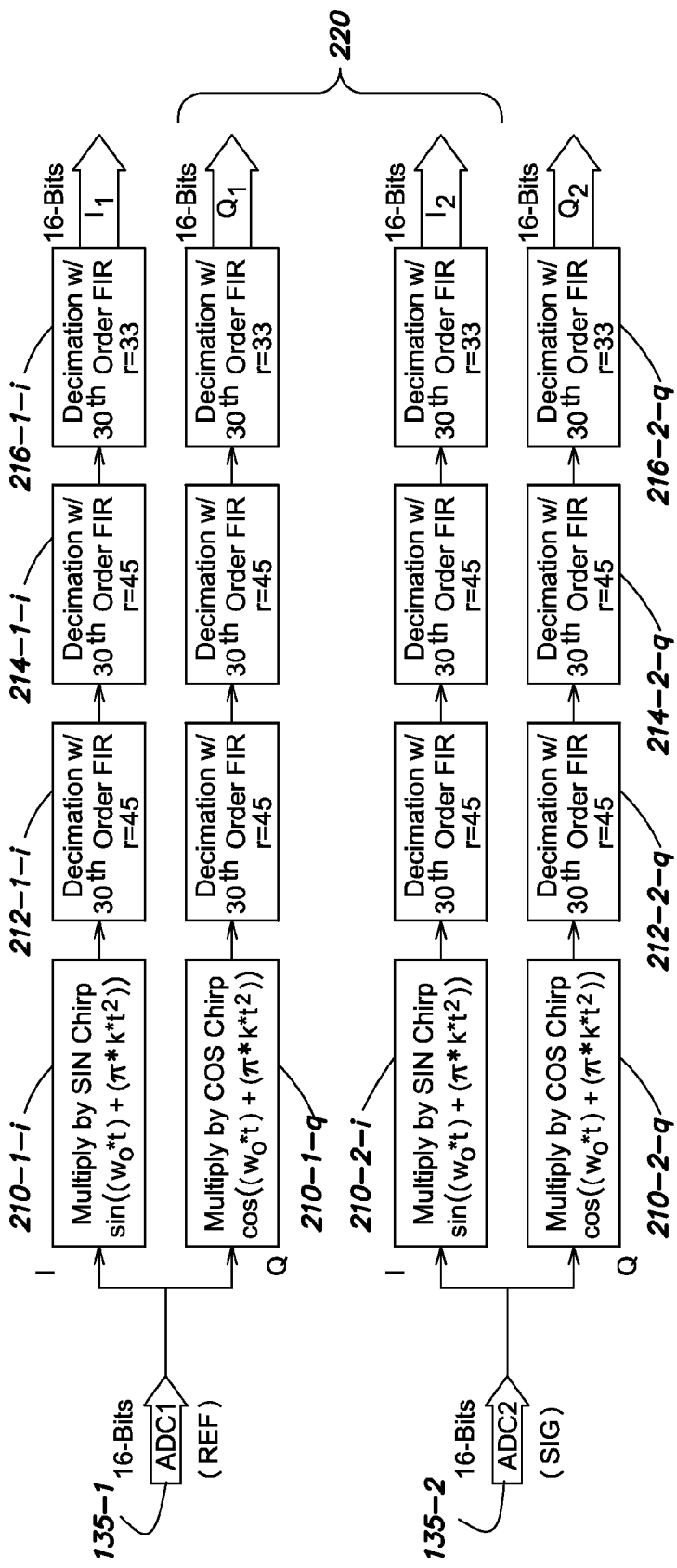
FIG. 2 is a detailed view of digital down-conversion.

FIG. 2 shows a first part of the receive processing, namely down-conversion with de-chirping. ADC1 135-1 and ADC2 135-2 receive and convert, respectively, the REF and SIG signals from the coupler 120. IN the example shown, the ADCs 135 are 16-bits wide. The digitized signals are dechirped by multiplying the respective receive signals by the corresponding chirp signals used by the transmitter. Multiplying each of the REF and SIG by corresponding sine and cosine provides in phase and quadrature (I and Q) channels for each of the REF and SIG signals Thus, the four dechirping blocks 210-1-$i$, 210-1-$q$, 210-2-$i$, 210-2-$q$ are needed to provide these four channels.

Next applied are one or more stages of decimation functions 212, 214, 216 applied to each of the four channels (I and Q for each of SIG and REF). The decimation may also apply a finite impulse response (FIR) filter to the dechirped data. The decimation function(s) reduce the original sampling rate for the receive signals to a lower rate. The decimation processes also low-pass filter the receive signal data, and then re-samples the resulting filtered signal at a lower rate. The decimate functions 212 may for example use an order 30 FIR filter with a cutoff frequency of 1/r and may be implemented for example as the "fir1" algorithm known in Matlab. The result is 16 bit wide decimated and filtered data 220 for the four channels (again, I and Q for each of the REF and SIG channels).

Figure 3:
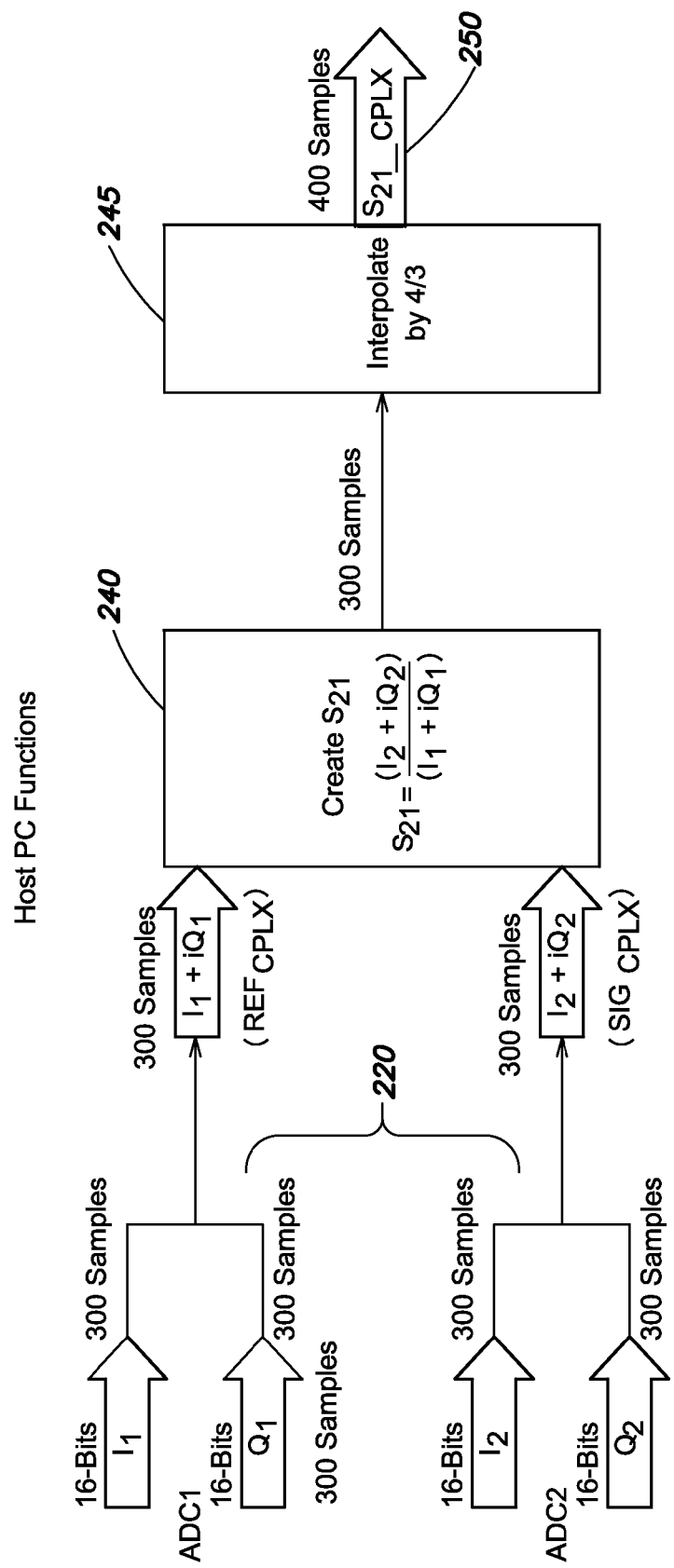
FIG. 3 shows host computer/signal processor functions.

The decimated and filtered data channels 220 are then provided to the next function as shown in FIG. 3. The next step is to create S21 parameters 240 by determining a complex-valued ratio of the SIG to REF signals for the receive sampled sequences, in groups of samples such as 300 samples. The notations using CPLX in the subscripts $REF_{CPLX}$ and $SIG_{CPLX}$ indicate that the I and Q portions of each of the REF and SIG channels are combined here represented as a complex signal. The S21 parameters are determined from $$REF_{CPLX} = (I_1 + Q_1)$$

$$SIG_{CPLX} = (I_2 + Q_2)$$

so that $$S_{21} = \frac{(I_2 + Q_2)}{(I_1 + Q_1)}$$

The S21 parameters may then be further interpolated 245 by a factor, such as 4/3 to provide an $S_{21\_CPLX}$ output signal 250 in groups of 400 samples.

Figure 4:
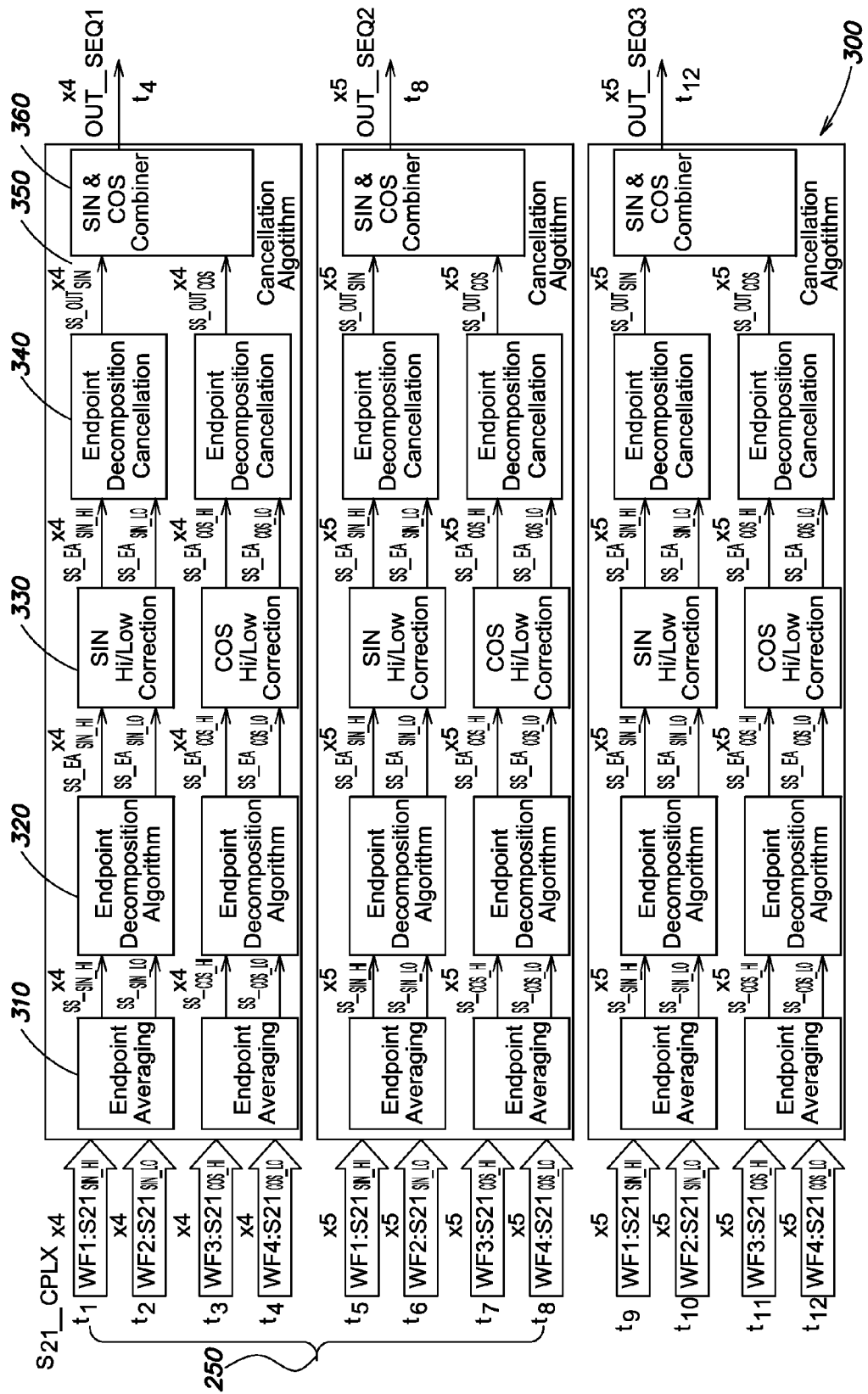
FIG. 4 shows a cancellation algorithm.

FIG. 4 illustrates a sequence of functions to perform cancellation 300. It is understood that the cancellation 300 functions is only shown for one of the characteristic NQR frequencies of interest. The system 100 therefore performs the functions shown in FIG. 4 for each characteristic NQR emission frequency for each material of interest. Keep in mind that an RF chirp is also emitted with two different phases (SIN and COS) and two different power levels (HI and LOW) for each frequency, and that there may be three or more characteristic frequencies of interest for a given material. In this embodiment, then there are 12 time slots, $t_1, t_2, \ldots, t_{12}$ made available for receiving the 12 possible different emitted chirp signals associated with a given material of interest.

The cancellation function removes the incident field from the NQR response, allowing the receive signal to be processed while the system is transmitting.

As described in the patent applications incorporated by reference above, receive signals corresponding to sine (SIN) and cosine (COS) chirps for each frequency of interest are emitted at respective high (HI) and low (LO) power levels. Thus for each characteristic frequency of interest there are four resulting received signals labeled WF1, WF2, WF3 and WF4 fed to the cancellation algorithm. "WF1" is S21 for the SIN chirp emitted at high power; "WF2" is S21 for the SIN chirps at low power; "WF3" is S21 for the COS chirp at high power; and "WF4" is s21 for the COS chirp emitted at low power.

Figure 8:
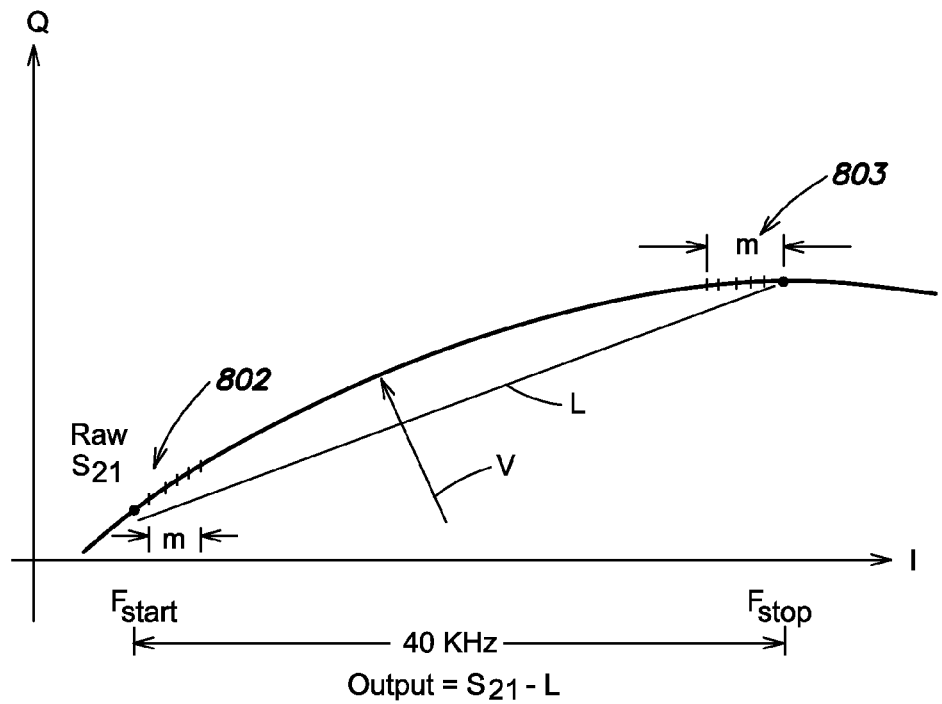
FIG. 8 shows more detail of end point averaging.

A first step in cancellation 300 is to apply end point averaging 310, as described in more detail below in connection with FIG. 8. This provides adjusted data to an end point decomposition function 320. A third step as part of cancellation 300 is to apply high and low power correction 330. This function compares the signal received at high power with that received at low power for each of the SIN and COS channels. End point cancellation 340 then provide the corrected SIN and COS outputs 350. Finally, a combiner 360 provides a complex valued output sequence by combining the SIN and COS channels for each one of the NQR frequencies of interest. In this example, there will be up to three such sequences, OUT_SEQ1, OUT_SEQ2, and OUT_SEQ3 for each of the three frequencies corresponding to a material of interest.

Figure 5:
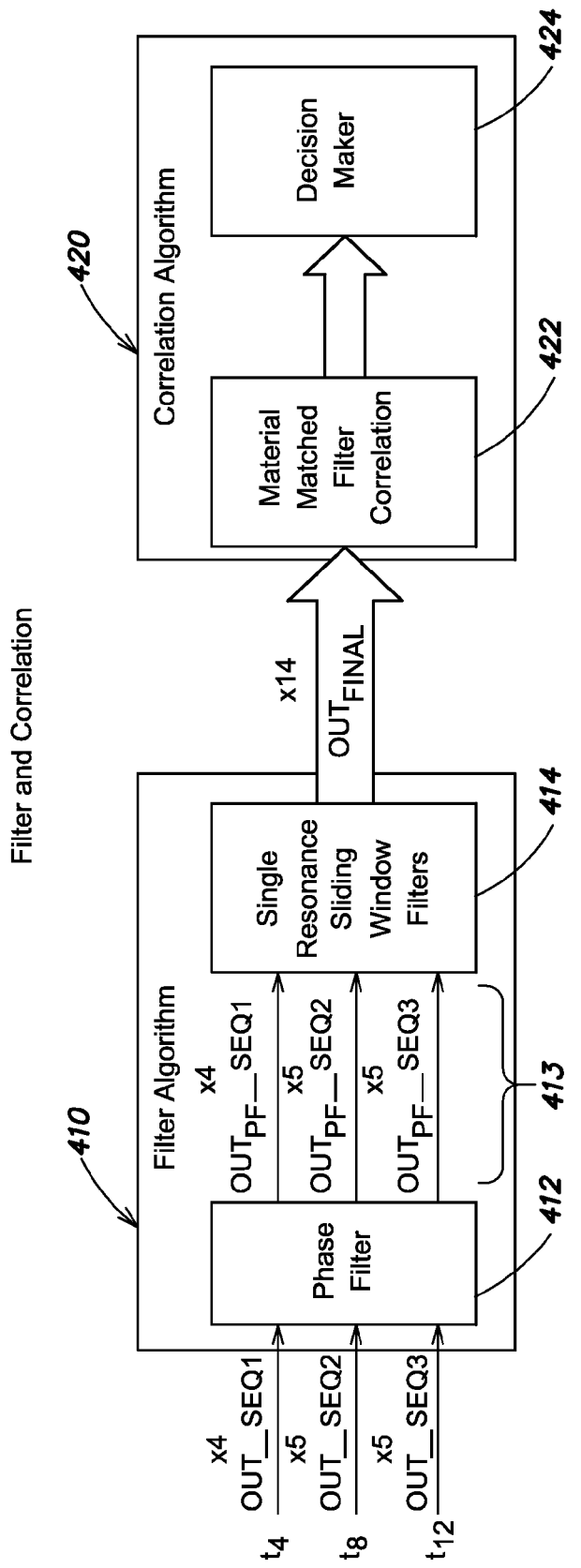
FIG. 5 is a detailed view of filtering and correlation functions.

FIG. 5 illustrates a final filter 410 and correlation 420 functions. The final filter 410 may accept as input all three outputs from the three expected characteristic frequency responses for a particular material. In the illustrated example, these occurred as outputs OUT_SEQ1, OUT_SEQ2 and OUT_SEQ3. These may be first fed to a phase filter 412 that can be a single resonance sliding window filter unique to each expected resonance. This filter 412 can remove the effect of the location (e.g., the relative height) of the material of interest within the portal—which affects the resulting phase of the received signal. The phase processed signals 413 may then be applied to a single resonance, sliding window filter 414 to remove this artifact, to produce a final output signal $OUT_{FINAL}$.

The correlation algorithm 420 then applies a matched filter 422 to the final output signal. The matched filter correlates each response against a library of templates of expected responses for each frequency of interest, feeding that output to a decision maker 424. The decision maker compares each matched filter output, for example, against a threshold, to make a determination as to whether the material was detected.

The PC may then provide an alert to an operator of the system.

Figure 6:
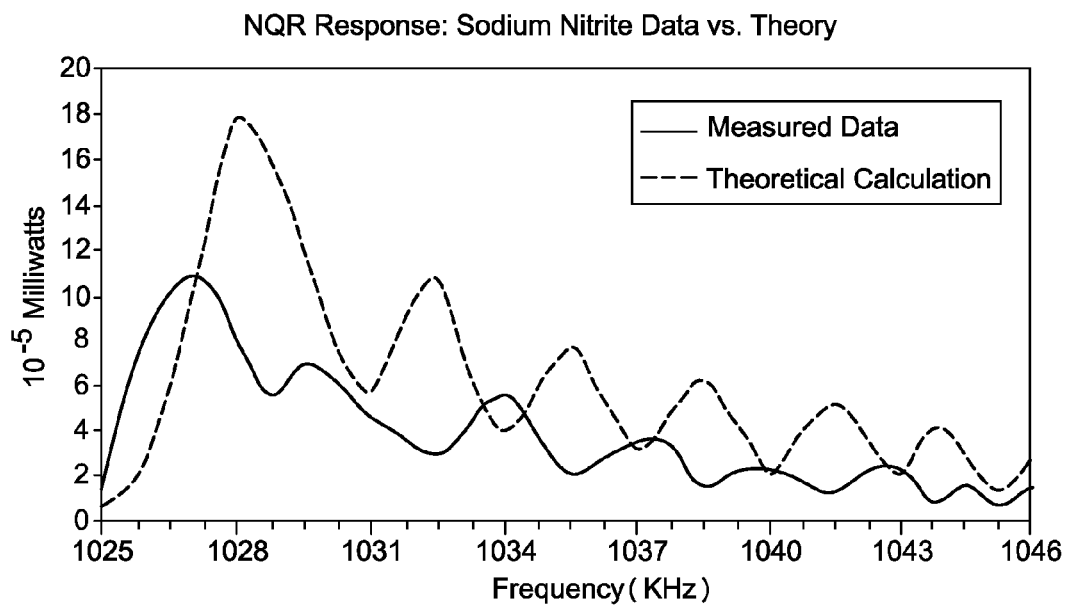
FIG. 6 is a typical NQR response for sodium nitrate.
Figure 7:
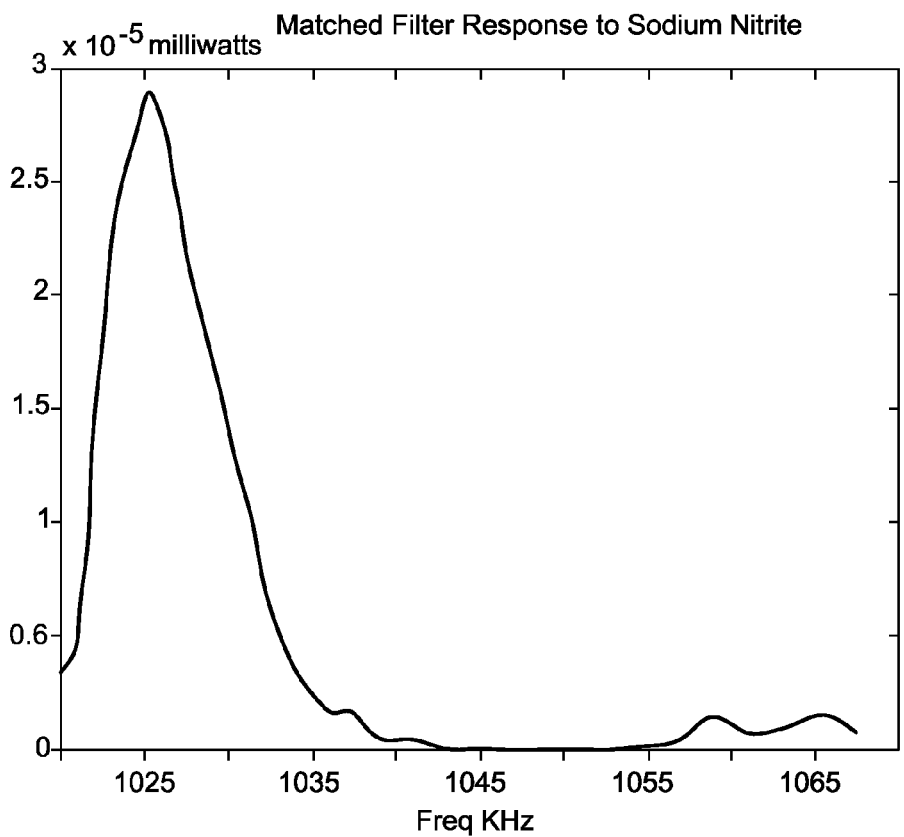
FIG. 7 is a resulting matched filter response.

An example of the improvement available or possible with the application of a matched filter 422 is shown in FIGS. 6 and 7.

The NQR response signal shown in FIG. 6 is seen to contain a sudden increase followed by decaying oscillations. Furthermore, the phase of the signal (not shown) is relatively flat because of the stimulated emission in the coherence of the Rabi oscillations.

The characteristic shape, the decaying oscillations due to the Rabi transitions, and the flat phase are utilized to create the matched filter 422. The characteristics of the matched filter 422 are designated by a frequency domain representation of the time domain response of FIG. 6. For example, the matched filter transfer function is the complex conjugate of the spectrum assuming a white Gaussian noise model for interfering signals. The matched filter 422 operations can be performed by fast convolution using Fast Fourier Transforms. If the interfering noise is not white, but can be described by some other power density spectrum, then the matched filter transfer function can be the complex conjugate of the frequency domain representation divided by that other noise spectrum.

A typical expected matched filter output corresponding to the NQR response of FIG. 6 is shown in FIG. 7. The particular example response was to sodium nitrite but the same principles can be applied to other materials and other responses.

Returning attention to FIG. 4, one preferred implementation of the end point decomposition 320 will now be described in more detail. FIG. 8 is an example plot of the raw S21 data samples 250 provided to the end point averaging function 310. Here, start 802 and stop 803 endpoints are chosen from the raw S21 data to determine how the remaining S21 samples are integrated. In the example shown, the chirp was a 40 kiloHertz (40 kHz) sweep from Fstart to Fstop, encompassing at least one potential NQR emission frequency of interest. The raw S21 data (whether it be for the empty portal, the low power measurement or the high power measurement, sine or cosine, etc.) may be represented a vector magnitude and frequency (angle) on an I and Q complex-valued plane, with the raw response manifesting itself as moving vector V in the complex plane.

An interpolated line segment, L, is developed from the end points of the raw S21 data. The interpolated line segment L is then compared to the raw s21 measured values, for example, to determine the output of S21 decomposition 320 as the difference between the S21 measurement and the corresponding segment L.

Here, the two raw data values measured at the exact endpoints, Fstart and Fstop, of the swept range are not used directly. Rather, a small subset of points near each of Fstart and Fstop, which may be "m" such points, are first averaged. The average of those respective sets of "m" points is then taken as the respective points to determine the linear segment L. In the specific example discussed here, "m" may be five (5). Thus an average is taken of the five (5) raw S21 data points taken near Fstart, and an average is taken of the five (5) S21 data points taken near Fend, to determine the line segment L.

With such end point integration, the resulting output has been found to be more accurate.

We have also found that a still further improvement can be obtained in situations where the signal to noise ratio is marginal. In particular, when the probability of false alarm and probability of detection in decision maker 424 are non-optimal, an initial measurement may first be taken. When the result is determined to be non-optimal, the measurements can be repeated at double the original power levels, that is, the LO and HI power, SIN and COS, measurements are repeated at the still higher power levels. Since the signal to noise ratio is a function of the amplifier power squared, doubling the radiated power in the second pass (for each of the human at low power and human at high power measurements) may add 6 dB to the signal to noise ratio. This can lead to higher quality results in marginal situations.

Figure 9:
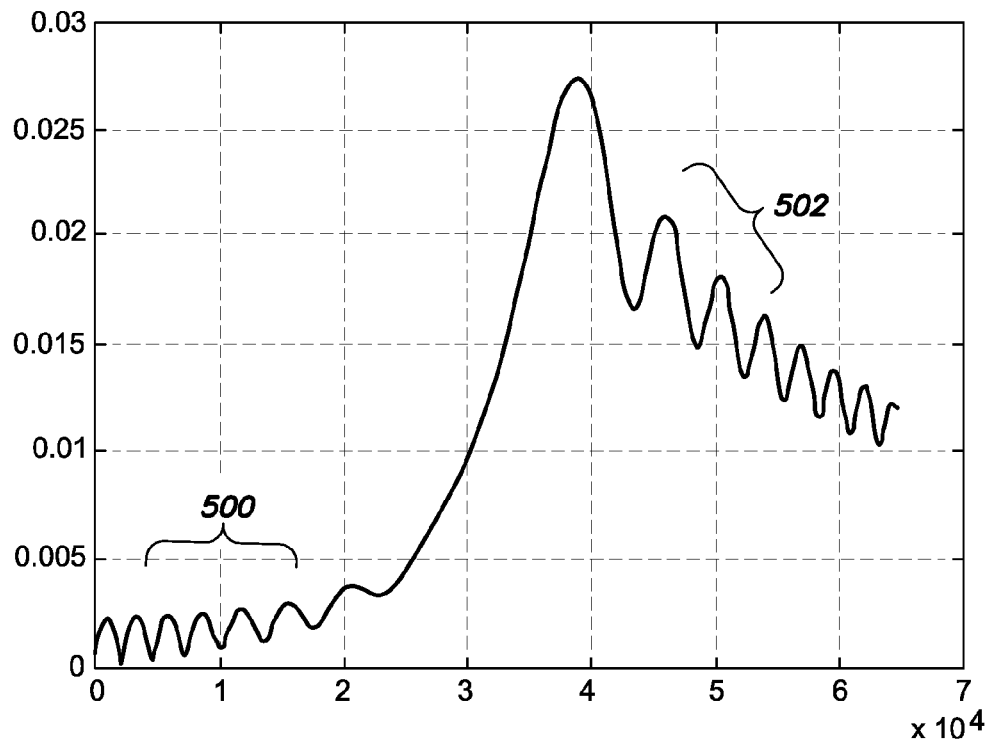
FIG. 9 is a matched filter response having Rabi oscillations.

It is also possible to use a matched filter response that more precisely accommodates the expected Rabi oscillations in the NQR response to a chirp waveform. An example of such a response is shown in FIG. 9. The response to an input chirp waveform exhibit Rabi oscillations 500, 502 manifested with a unique phase across the response. A suitable matched filter is therefore synthesized by transforming the illustrated time domain response waveform into the frequency domain for convolution.

The matched filter 422 then implements frequency domain convolution by multiplying a candidate received data set ($OUT_{final}$) by the frequency domain representation of the expected NQR response with Rabi oscillations. That product is then transformed back into the time domain. A correlation peak should therefore be present only if there is an NQR resonance present in the candidate data set.

In yet another approach, two NQR resonances of interest may be simultaneously excited by emitting two simultaneous radio frequency chirps. In this arrangement, the two simultaneous chirps include at least, two frequencies of interest for a particular material. The resulting emission may include not only the two expected NQR responses, but also an NQR response signal at a third frequency characteristic of that material of interest.

This approach avoids the need to generate and transmit an excitation waveform at the third frequency. Thus the cancellation algorithm (such as shown in FIG. 4) for the third frequency is not required to correctly detect the material. More particularly, because there is no incident emitted wave at the third frequency, correct detection of the material does not require cancellation processing at the third frequency. The third frequency resonance response is expected to have a signal strength of about 50% that of the single resonance.

The fact that no cancellation is required to detect the NQR signal means that the 90 odd db of dynamic range typically used to perform the cancellation operation can be used to detect smaller signals at a distance. For example, using the radar range equation it is can be shown that at a range of 100 feet the NQR signal to noise ratio will be equal to the signal to noise observed in the portal if the power amplifier output is 50 watts.

What is claimed is:

1. An apparatus comprising:
a portal, defined by one or more conductive surfaces;
at least one wire loop, disposed adjacent one or more of the conductive surfaces;
a radio frequency transmitter, to generate a plurality of time varying electromagnetic fields within the portal, the electromagnetic fields induced by two or more chirped radio frequency signals at selected phases, selected power levels, and selected chirp start and chirp stop frequencies that include nuclear quadrupole resonant frequencies (NQR) of a material of interest;
a coupler coupled to the radio frequency transmitter at an input port, to the at least one wire loop at an output port, and to a receiver at both a signal port and a reference port, the receiver signal port providing a signal (SIG) representing quadrupole resonant emissions from a substance within the portal, and the receiver reference port providing a reference (REF) representative of the output of the radio frequency transmitter; and a signal processor, for further processing signals received on the receiver reference and signal ports, the processor further providing:
a downconverter, for downconverting the SIG and REF signals using chirp signals with corresponding phases used by the transmitter, and providing downconverted SIG and REF signals;
a decimator, for decimating the downconverted SIG and REF signals, to provide decimated SIG and REF signals;
an S21 parameter estimator, for operating on the SIG and REF signals to provide S21 parameter sample set estimates, wherein the S21 parameter is a complex-valued ratio of the SIG and REF signals;
an end point decomposition function, for operating on endpoints of the S21 parameter sample sets, to determine average values of samples adjacent the endpoints, and to further determine an interpolation by which the S21 parameter sample sets are further adjusted, to provide decomposition samples;
a phase filter, for operating on the decomposition samples, to provide filtered received samples; and
a matched filter correlator, for matched filtering the received samples against an expected NQR frequency response.

2. The apparatus of claim 1 additionally wherein:
the radio frequency transmitter transmits chirped radio frequency signals including a sine phase (SIN), cosine phase (COS), a high power level (HI), and low power level (LO), with a selected radio frequency.

3. The apparatus of claim 2 additionally wherein:
a combiner combines decomposition samples received for corresponding chirped radio frequency signals including SIN and COS for the selected frequency.

4. The apparatus of claim 1 additionally wherein:
the matched filter correlator matches the received samples against an NQR response signal that includes induced oscillations.

5. The apparatus of claim 1 additionally wherein the end point decomposition further:
determines two raw data values corresponding to endpoints, Fstart and Fstop, of a chirp range;
selects a subset of data values near each of the endpoints Fstart and Fstop;
determines an average the respective subsets of data values taken as the respective end points to determine averaged endpoints that define a linear segment L;
adjusting the raw data values by comparing them to linear segment L.

6. The apparatus of claim 1 wherein the phase filter is a single frequency sliding window filter.

7. The apparatus of claim 4 wherein the matched filter further comprises a transfer function that includes a noise estimate.

8. The apparatus of claim 1 wherein the phase filter is a single frequency sliding window filter.

9. The apparatus of claim 1 additionally wherein:
the radio frequency transmitter emits a time varying electromagnetic field with a first radio frequency chirp that includes a first frequency, and simultaneously emits a second radio frequency chirp that includes a second frequency that is different from the first frequency; and
the signal processor operates on a response signal received at a third frequency in response to said first and second chirps, wherein said third frequency response signal is defined by nuclear quadrupole resonance of a material of interest.

10. The apparatus of claim 9 wherein the signal processor omits at least one of the downconverter, decimator, S21 parameter estimator, end point decomposition, or phase filter during processing of the third frequency response signal.

* * * * *

UNITED STATES PATENT AND TRADEMARK OFFICE
CERTIFICATE OF CORRECTION

| | | |
|---|---|---|
| PATENT NO. | : 9,052,370 B2 | Page 1 of 1 |
| APPLICATION NO. | : 14/206394 | |
| DATED | : June 9, 2015 | |
| INVENTOR(S) | : John T. Apostolos et al. | |

It is certified that error appears in the above-identified patent and that said Letters Patent is hereby corrected as shown below:

In the Specification:
Col. 1, line 53 should read:
emissions. It therefore becomes desirable to design the Col. 3, line 5 should read:
110 (DAC1 to DAC6) and analog to digital converters 135

Col. 3, line 54 should read:
needed to detect certain materials are described in more Col. 7, line 43 should read:
radar range equation it can be shown that at a range of 100

Signed and Sealed this
Third Day of November, 2015

Michelle K. Lee
*Director of the United States Patent and Trademark Office*